United States Patent
Martin et al.

(10) Patent No.: US 9,480,789 B2
(45) Date of Patent: Nov. 1, 2016

(54) METHOD AND SEDATION DELIVERY SYSTEM INCLUDING A PUMP ASSEMBLY AND A CO-FORMULATION OF FIRST AND SECOND DRUGS

(75) Inventors: James F. Martin, Lebanon, OH (US); Paul Bruggeman, Loveland, OH (US)

(73) Assignee: ETHICON ENDO-SURGERY, INC., Cincinnati, OH (US)

( * ) Notice: Subject to any disclaimer, the term of this patent is extended or adjusted under 35 U.S.C. 154(b) by 2016 days.

(21) Appl. No.: 12/475,697

(22) Filed: Jun. 1, 2009

(65) Prior Publication Data

US 2010/0300438 A1     Dec. 2, 2010

(51) Int. Cl.
*A61M 5/142* (2006.01)
*A61M 5/168* (2006.01)
*G06F 19/00* (2011.01)

(52) U.S. Cl.
CPC ......... *A61M 5/142* (2013.01); *A61M 5/16827* (2013.01); *G06F 19/3468* (2013.01); *A61M 2205/6009* (2013.01); *A61M 2205/6018* (2013.01); *A61M 2205/6054* (2013.01); *A61M 2205/6063* (2013.01); *A61M 2205/6072* (2013.01)

(58) Field of Classification Search
CPC ............ A61M 2205/6009; A61M 2205/6018; A61M 2205/6054; A61M 2205/6063; A61M 2205/6072; A61M 5/142; A61M 5/16827; G06F 19/3468
USPC ......... 128/203.14; 514/649, 329; 235/462.01
See application file for complete search history.

(56) References Cited

U.S. PATENT DOCUMENTS

| | | |
|---|---|---|
| 4,060,079 A | 11/1977 | Reinhold, Jr. |
| 4,513,866 A | 4/1985 | Thomas |
| 4,739,913 A | 4/1988 | Moore |
| 5,293,913 A | 3/1994 | Preszler |
| 5,530,531 A | 6/1996 | Girard |

(Continued)

FOREIGN PATENT DOCUMENTS

| | | |
|---|---|---|
| DE | 102007010326 | 9/2008 |
| JP | 2001-509059 (A) | 7/2001 |

(Continued)

OTHER PUBLICATIONS

PCT, International Search Report, International Application No. PCT/US2010/036049 (Dec. 7, 2010).

(Continued)

*Primary Examiner* — Imani Hayman
(74) *Attorney, Agent, or Firm* — Thompson Hine LLP

(57) ABSTRACT

A drug delivery system includes drug containers, a pump assembly, a sensor, and a controller. The drug containers each contain a different predetermined drug co-formulation of predetermined first and second drugs, wherein the first drug has a sedative effect. The sensor is adapted to sense a variable associated with the drug containers and output a different drug co-formulation identification signal associated with each of the drug containers based on the sensed variable. The controller is programmed to identify the drug co-formulation for the drug container operatively connected to the pump assembly from the associated identification signal and to control the pump assembly to deliver the drug co-formulation of the one drug container to the patient during a medical procedure according to a corresponding drug delivery algorithm which is different for each of the drug containers. A method is also disclosed which uses the drug delivery system.

20 Claims, 2 Drawing Sheets

(56) References Cited

U.S. PATENT DOCUMENTS

| | | | |
|---|---|---|---|
| 5,573,154 | A | 11/1996 | Tietze |
| 5,626,151 | A | 5/1997 | Linden |
| 5,807,316 | A | 9/1998 | Teeple, Jr. |
| 5,925,014 | A * | 7/1999 | Teeple, Jr. .................. 358/1.15 |
| 5,971,148 | A | 10/1999 | Jackson |
| 5,975,081 | A | 11/1999 | Hood et al. |
| 6,000,395 | A | 12/1999 | Brown |
| 6,043,273 | A | 3/2000 | Duhaylongsod |
| 6,071,933 | A | 6/2000 | Joo et al. |
| 6,182,667 | B1 | 2/2001 | Hanks et al. |
| 6,354,477 | B1 | 3/2002 | Trummer |
| 6,409,745 | B1 | 6/2002 | Ducharme et al. |
| 6,412,482 | B1 | 7/2002 | Rowe |
| 6,450,166 | B1 | 9/2002 | McDonald et al. |
| 6,651,658 | B1 | 11/2003 | Hill et al. |
| 6,899,103 | B1 | 5/2005 | Hood et al. |
| 6,929,041 | B2 | 8/2005 | Falligant et al. |
| 6,958,691 | B1 | 10/2005 | Anderson et al. |
| 7,229,430 | B2 | 6/2007 | Hickle et al. |
| 7,438,072 | B2 | 10/2008 | Izuchuksu |
| 7,657,956 | B2 | 2/2010 | Stacy et al. |
| 7,818,840 | B2 | 10/2010 | Barnett et al. |
| 7,970,631 | B2 | 6/2011 | Bruggeman et al. |
| 2002/0017299 | A1 | 2/2002 | Hickle |
| 2003/0040700 | A1 | 2/2003 | Hickle et al. |
| 2003/0074223 | A1 | 4/2003 | Hickle et al. |
| 2004/0073177 | A1 | 4/2004 | Hickle |
| 2004/0103897 | A1 | 6/2004 | Hickle et al. |
| 2004/0134494 | A1 | 7/2004 | Papania et al. |
| 2005/0011916 | A1 | 1/2005 | Battista |
| 2005/0177096 | A1 | 8/2005 | Bollish |
| 2006/0009734 | A1 | 1/2006 | Martin |
| 2006/0042633 | A1 | 3/2006 | Bishop et al. |
| 2006/0100574 | A1 | 5/2006 | Izumi et al. |
| 2006/0206356 | A1 | 9/2006 | Vanderveen |
| 2007/0088271 | A1 | 4/2007 | Richards |
| 2007/0191789 | A1 | 8/2007 | Hickle |
| 2007/0191817 | A1* | 8/2007 | Martin ....................... 604/890.1 |
| 2007/0197978 | A1 | 8/2007 | Wortham |
| 2007/0276270 | A1 | 11/2007 | Tran |
| 2008/0275425 | A1 | 11/2008 | Strickler et al. |
| 2008/0302623 | A1 | 12/2008 | Gupton, Jr. |
| 2009/0099552 | A1 | 4/2009 | Levy et al. |
| 2010/0010321 | A1 | 1/2010 | Foster |
| 2010/0010433 | A1 | 1/2010 | Krogh et al. |
| 2010/0038317 | A1 | 2/2010 | Bissler et al. |
| 2010/0137828 | A1 | 6/2010 | Michard et al. |
| 2010/0268065 | A1 | 10/2010 | Pile-Spellman et al. |

FOREIGN PATENT DOCUMENTS

| | | |
|---|---|---|
| JP | 2004-166847 (A) | 6/2004 |
| JP | 2004-194877 (A) | 7/2004 |
| JP | 2005-503202 (A) | 2/2005 |
| JP | 2005-509465 (A) | 4/2005 |
| JP | 2005-525885 (A) | 9/2005 |
| JP | 2006-511253 (A) | 4/2006 |
| JP | 2008-505692 (A) | 2/2008 |
| JP | 2008-532635 (A) | 8/2008 |
| JP | 2009-082183 (A) | 4/2009 |
| WO | 2004/078033 | 9/2004 |
| WO | 2007/061368 | 5/2007 |

OTHER PUBLICATIONS

ECRI: "Patient-controlled analgesic infusion pump," *Health Devices* vol. 35. No. 1, pp. 5-35 (Jan. 1, 2006).

ECRI: "General-Purpose Infusion Pumps," *Health Devices*, vol. 36, No. 10, pp. 309-336 (Oct. 1, 2007).

Le Couteur, C., "Intensive Care" E. NZ Magazine, Institute of Professional Engineers, New Zealand, vol. 6, No. 6, pp. 26-29 (Nov. 1, 2005).

US, Office Action, U.S. Appl. No. 12/506,385; 16 pages (Apr. 29, 2010).

PCT, International Search Report, International Application No. PCT/US2009/049934; 8 pages (Mar. 10, 2010).

PCT, International Preliminary Report on Patentability, International Application No. PCT/US2010/036049 (Dec. 6, 2011).

CN, Notification of the First Office Action (English Translation), Chinese Patent Application No. 201080032635.X, Dec. 19, 2013.

JP, Notification of Reasons for Refusal (English Translation), Japanese Patent Application No. 2012-513980, Feb. 18, 2014.

NZ, Examination Report, New Zealand Patent Application No. 596582, Oct. 18, 2012.

* cited by examiner

METHOD AND SEDATION DELIVERY SYSTEM INCLUDING A PUMP ASSEMBLY AND A CO-FORMULATION OF FIRST AND SECOND DRUGS

FIELD OF THE INVENTION

The present invention is related generally to medical technology, and more particularly to a method and to a sedation delivery system including a pump assembly and a co-formulation of first and second drugs.

BACKGROUND OF THE INVENTION

Known sedation delivery systems include drug-delivery conscious sedation systems. A known drug-delivery conscious sedation system is disclosed in United States Patent Application Publication No. 2002/0017299. In that system, a controller analyzed physiological parameters of the patient (such as blood pressure, etc.) and generated a request for a predetermined response from a patient. The controller analyzed the time delay between the request and the response to determine a level of sedation of the patient. When the time delay between the request and the response increased, the controller determined that the patient was in a deeper level of sedation and decreased the flow of a conscious sedation drug to the patient.

It is known to administer a pre-procedure single bolus of fentanyl (a drug having an analgesic effect) to a patient 2-3 minutes before the start of an infusion of propofol (a drug having a sedative effect) to the patient for a conscious (AKA minimal-to-moderate) sedation procedure.

U.S. Pat. No. 6,071,933 discloses several co-formulations (i.e., fixed combinations) of propofol and remifentanil (a drug having an analgesic and a sedative effect) used for patient-controlled anesthesia.

Still, scientists and engineers continue to seek improved methods and sedation delivery systems having a pump assembly and a co-formulation of first and second drugs.

SUMMARY OF THE INVENTION

A first expression of an embodiment of the invention is for a drug delivery system including a plurality of drug containers, a pump assembly, a sensor, and a controller. The drug containers each contain a different predetermined drug co-formulation or fixed combination of predetermined first and second drugs, wherein the first drug has a sedative effect. Each of the drug containers is operatively connectable to the pump assembly, and the pump assembly is adapted to deliver the drug co-formulation contained in an operatively-connected one of the drug containers to a patient during a medical procedure. The sensor is adapted to sense a variable associated with each of the drug containers and output a different drug co-formulation identification signal associated with each of the drug containers based on the sensed variable. The controller is operatively connected to the sensor and to the pump assembly. The controller is programmed to identify the drug co-formulation for the operatively-connected one of the drug containers from the associated identification signal and to control the pump assembly to deliver the drug co-formulation of the operatively-connected one of the drug containers to the patient during the medical procedure according to a corresponding drug delivery algorithm which is different for each of the drug containers.

A second expression of a first embodiment of the invention is for a drug delivery system including a plurality of drug containers, a pump assembly, a sensor, and a controller. The drug containers each contain a different predetermined drug co-formulation of predetermined first and second drugs. The first drug has a sedative effect, and the second drug has an analgesic effect. The different predetermined drug co-formulations also include co-formulations that include at least two or four different drugs. Each of the drug containers is operatively connectable to the pump assembly. One of the drug containers is operatively connected to the pump assembly, and the pump assembly is adapted to deliver the drug co-formulation contained in the operatively-connected one of the drug containers to a patient during a medical procedure. The sensor is adapted to sense a variable associated with each of the drug containers and output a different drug co-formulation identification signal associated with each of the drug containers based on the sensed variable. The controller is operatively connected to the sensor and to the pump assembly. The controller is programmed to identify the drug co-formulation for the operatively-connected one of the drug containers from the associated identification signal and to control the pump assembly to deliver the drug co-formulation of the operatively-connected one of the drug containers to the patient during the medical procedure according to a corresponding drug delivery algorithm which is different for each of the drug containers.

A method of the invention is for delivering drugs to patients during medical procedures using the drug delivery system of the previously-described first expression of the embodiment of the invention, wherein the plurality of drug containers includes at least four drug containers, wherein the at-least-four drug containers includes first and second drug containers, and wherein the method includes steps a) through i). Step a) includes choosing the first drug container based on a first medical procedure and an assessment of a patient associated with the first medical procedure. Step b) includes having the sensor sense the variable associated with the first drug container and output the identification signal associated with the first drug container. Step c) includes having the controller automatically determine a first drug delivery algorithm based on the identification signal associated with the first drug container. Step d) includes having the controller control the pump assembly to deliver the drug co-formulation of the first drug container to the patient associated with the first medical procedure based at least on the first drug delivery algorithm. Step e) includes choosing the second drug container based on a second medical procedure and an assessment of a patient associated with the second medical procedure, wherein at least one of the second medical procedure and the patient associated with the second medical procedure is different from the corresponding one of the first medical procedure and the patient associated with the first medical procedure. Step f) includes having the sensor sense the variable associated with the second drug container and output the identification signal associated with the second drug container. Step g) includes having the controller automatically determine a second drug delivery algorithm based on the identification signal associated with the second drug container, wherein the second drug delivery algorithm is different from the first drug delivery algorithm. Step h) includes having the controller control the pump assembly to deliver the drug co-formulation of the second drug container to the patient associated with the second medical procedure based at least on the second drug delivery algorithm.

Several benefits and advantages are obtained from one or more of the method and expressions of an embodiment of the invention. In one example, having different co-formulations (fixed combinations) of a first drug having a sedative effect and a second drug having an analgesic effect allows the user to choose a particular co-formulation best suited to a particular medical procedure and a particular patient, wherein a sensor outputs a different drug co-formulation identification signal associated with each drug container avoiding human error, and wherein a controller automatically determines a particular drug delivery algorithm based on the identified particular co-formulation avoiding the time and human error of having the user determine or choose an algorithm.

DETAILED DESCRIPTION

Before explaining a method and several expressions of an embodiment of the invention in detail, it should be noted that each is not limited in its application or use to the details of construction and arrangement of parts, instructions, and steps illustrated in the accompanying drawings and description. The illustrative method and expressions of an embodiment of the invention may be implemented or incorporated in other methods, expressions, embodiments, variations, and modifications, and may be practiced or carried out in various ways. Furthermore, unless otherwise indicated, the terminology employed herein has been chosen for the purpose of describing the illustrative method and expressions of an embodiment of the present invention for the convenience of the reader and are not for the purpose of limiting the invention.

It is further understood that any one or more of the following-described expressions of a drug delivery system, implementations, etc. can be combined with any one or more of the other following-described expressions of a drug delivery system, implementations, etc.

Figure 1:
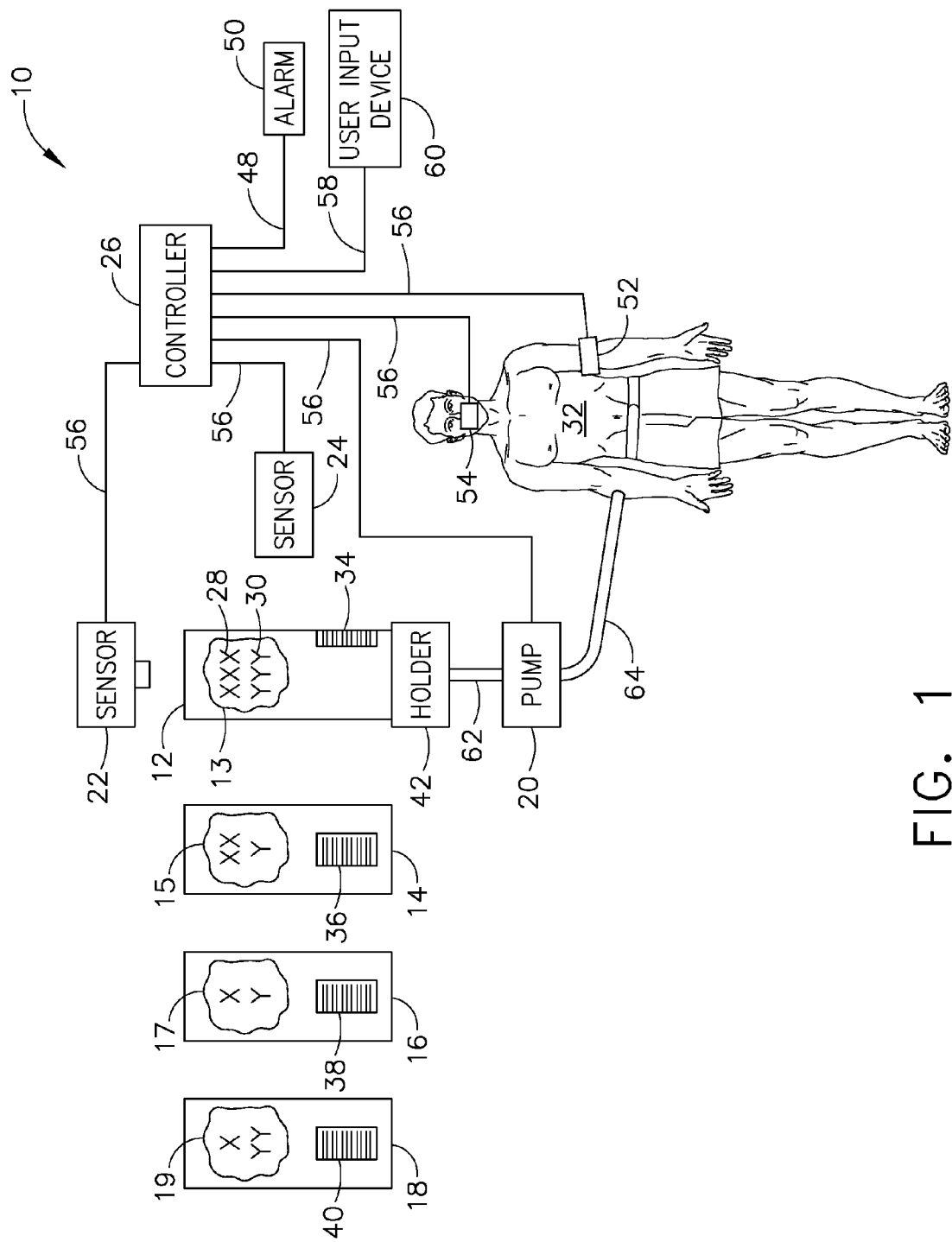
FIG. 1 is schematic diagram of an embodiment of a drug delivery system of the invention including four drug containers only one of which is operatively connected to the pump assembly, wherein the drug containers are shown partly in break-away to reveal the different co-formulations of the first and second drugs contained therein, and wherein the system includes a proximity sensor to sense the size of a drug container and a bar code sensor to sense (scan) the bar code of a drug container.

A first embodiment of the invention is shown in FIG. 1. A first expression of the embodiment of FIG. 1 is for a drug delivery system 10 including a plurality of drug containers 12, 14, 16, and 18, a pump assembly 20, a sensor (two are shown) 22 and 24, and a controller 26. The drug containers 12, 14, 16, and 18 each contain a different predetermined drug co-formulation 13, 15, 17, and 19 of predetermined first and second drugs 28 and 30 (wherein the first drug 28 is represented by an "x" and the second drug is represented by a "y" in FIG. 1 showing the different drug co-formulations [i.e., fixed combinations] 13, 15, 17, and 19 respectively contained in the drug containers 12, 14, 16, and 18). The first drug 28 has a sedative effect. Each of the drug containers 12, 14, 16, and 18 is operatively connectable to the pump assembly 20, and the pump assembly 20 is adapted to deliver the drug co-formulation 13 contained in an operatively-connected one of the drug containers 12 to a patient 32 during a medical procedure. The sensor 22 and 24 is adapted to sense a variable associated with each of the drug containers and output a different drug co-formulation identification signal associated with each of the drug containers 12, 14, 16, and 18 based on the sensed variable. The controller 26 is operatively connected to the sensor 22 and 24 and to the pump assembly 20. The controller 26 is programmed to identify the drug co-formulation 13 for the operatively-connected one of the drug containers 12 from the associated identification signal and to control the pump assembly 20 to deliver the drug co-formulation 13 of the operatively-connected one of the drug containers 12 to the patient 32 during the medical procedure according to a corresponding drug delivery algorithm which is different for each of the drug containers 12, 14, 16, and 18.

It is noted that each different drug co-formulation 13, 15, 17, and 19 of the first and second drugs 28 and 30 contains the same first drug 28 and the same second drug 30 but different fixed combinations thereof. In one realization of the first expression of the embodiment of FIG. 1, the drug containers 12, 14, 16, and 18 each are drug vials. Other types of drug containers include, without limitation, pre-filled drug syringes. It is also noted that, in one example, the sensor 22 and 24 is adapted to sense the variable after the associated drug container is operatively connected to the pump assembly 20. In another example, the variable is sensed before the associated drug container is operatively connected to the pump assembly 20.

In one implementation of the first expression of the embodiment of FIG. 1, the second drug 30 has an analgesic effect, and the medical procedure is a conscious sedation medical procedure. In one variation, the first drug 28 substantially lacks having an analgesic effect, and the second drug 30 substantially lacks having a sedative effect. In a different variation, the first drug also has another (e.g., analgesic) medical effect and/or the second drug also has another (e.g., sedative) medical effect. In a different implementation, not shown, the second drug has an amnesic effect. In one extension of the first expression of the embodiment of FIG. 1, not shown, one or more of the plurality of drug containers containing a different predetermined drug co-formulation of predetermined first and second drugs also includes at least a third drug which has a sedative, analgesic, amnesic, and/or other medical effect.

In one enablement of the first expression of the embodiment of FIG. 1, the different predetermined drug co-formulations 13, 15, 17, and 19 include at least first, second, third, and fourth drug co-formulations 13, 15, 17, and 19. In one example, the first drug co-formulation 13 includes 100 percent of a predetermined first amount of the first drug 28 and includes 0 percent of a predetermined second amount of the second drug 30. The second drug co-formulation 15 includes from 60 to 90 percent of the first amount of the first drug 28 and includes from 10 percent to 40 percent of the second amount of the second drug 30. In this example, the third drug co-formulation 17 includes from 10 percent to 40 percent of the first amount of the first drug 28 and includes from 60 percent to 90 percent of the second amount of the second drug 30. In another example depending on the drugs used, the four drug co-formulations may contain, respectively, 100% of the first drug and 0% of the second; 67% of the first drug and 33% of the second, 33% of the first drug and 67% of the second, and 0% of the first drug and 100% of the second.

In the same or a different enablement or example, the first and second drugs are chosen and different drug co-formulations are predetermined based on the pain stimulus of the procedure and the pain threshold or tolerance of the patient. In a different enablement or example, each drug co-formulation has 100 percent of a predetermined first amount of the first drug but has a different percent of a predetermined second amount of the second drug. Other enablements and examples are left to those skilled in the art.

In one illustration of the first expression of the embodiment of FIG. 1, the first drug 28 is propofol and the second drug 30 is ketamine. In a different illustration, the first drug 28 is propofol and the second drug 30 is remifentanil.

In a first application of the first expression of the embodiment of FIG. 1, the drug containers 12, 14, 16, and 18 each have a substantially same shape and a different size, and the sensor 22 senses the size. Here, the sensed variable is the different size of the drug container itself. In one example, the sensor 22 is a proximity sensor which senses the different lengths of the drug containers 12, 14, 16, and 18. In one construction, the sensor 22 is immovably disposed at a fixed distance and orientation with respect to the bottom of the operatively-connected tallest one of the drug containers 12.

In a second application of the first expression of the embodiment of FIG. 1, the drug delivery system 10 also includes a different bar code 34, 36, 38, and 40 associated with each of the drug containers 12, 14, 16, and 18, and the sensor 24 (such as a bar code scanner) is adapted to automatically sense (scan) the bar code 34 associated with the operatively-connected one of the drug containers 12. Here, the sensed variable is the different bar code associated with each drug container. In a first example, the sensor 24 is immovably disposed at a fixed distance and orientation with respect to the operatively-connected one of the drug containers 12, and the controller 26 periodically prompts the sensor 24 to scan an area where an expected bar code would be when a user operatively connects one of the drug containers 12, 14, 16, and 18 to the pump assembly 20 (such as by operatively connecting one of the drug containers 12, 14, 16, and 18 to a drug-container holder 42 which is operatively-connected to the pump assembly 20). In one configuration of the first example, not shown, each drug container and the drug-container holder are shaped so that the drug-container holder can only receive a drug container properly oriented to have its bar code sensed (scanned) by the sensor 24 when the bar code is on the drug container. In a second example, not shown, the sensor is a bar code scanner, wherein the user holds the sensor to scan the bar code or the user moves the bar code past the sensor.

Figure 2:
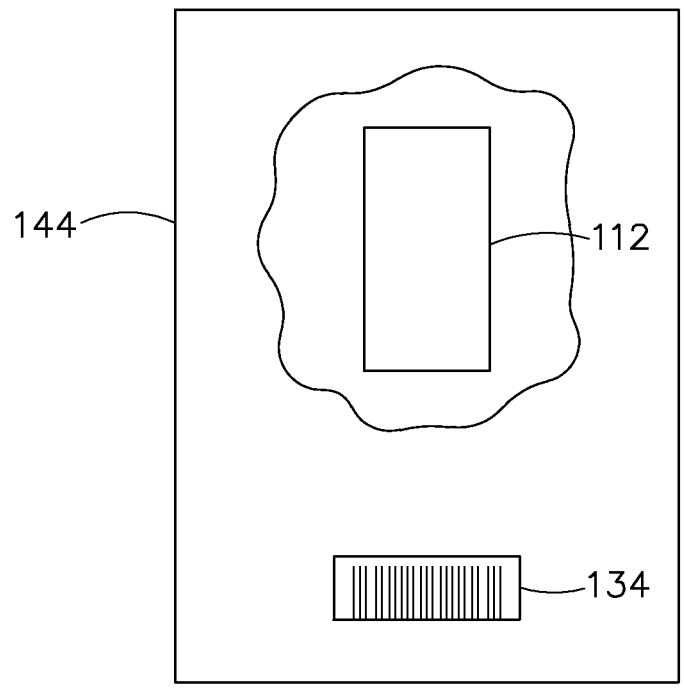
FIG. 2 is a schematic view of a first alternate bar code arrangement of the drug delivery system of FIG. 1, wherein the bar code is on a package shown partly in break-away to reveal the drug container therein.
Figure 3:
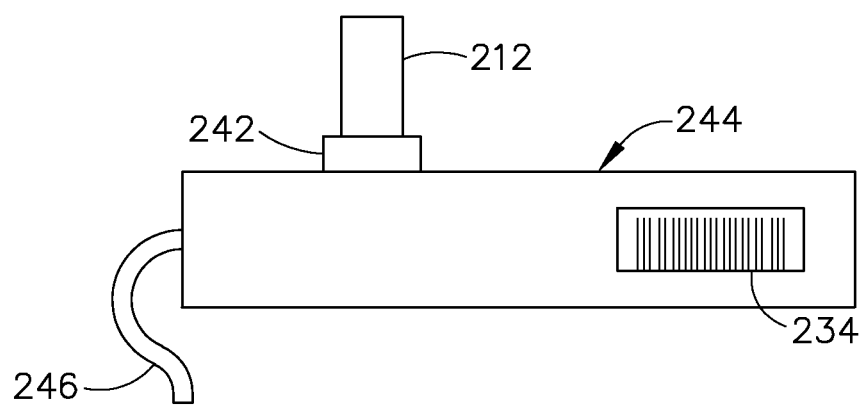
FIG. 3 is a schematic view of a second alternate bar code arrangement of the drug delivery system of FIG. 1, wherein the bar code is on a drug-delivery cassette, and wherein the cassette is installable in the pump assembly, includes a drug-container holder shown with an installed drug container, and includes tubing for making a fluid connection with the pump assembly.

In one bar code arrangement, as previously described, the different bar code 34, 36, 38, and 40 associated with each of the drug containers 12, 14, 16, and 18 is placed on the associated drug container 12, 14, 16, and 18. Here the sensed variable is the different bar code placed on the drug container. In a first alternate bar code arrangement, as seen in FIG. 2, the different bar code (e.g., bar code 134) associated with each of the drug containers (e.g., drug container 112) is placed on an associated drug-container package (e.g., drug-container package 144) containing the drug container (e.g., drug container 112). Here, the sensed variable is the different bar code of the package associated with the drug container. In one example, the package 144 is moved past the sensor 24 of FIG. 1, the package is opened to retrieve the drug container, and then the package 144 is discarded. In a second alternate bar code arrangement, as seen in FIG. 3, the different bar code (e.g., bar code 234) associated with each of the drug containers (e.g., drug container 212) is placed on an associated drug-delivery cassette (e.g., drug-delivery cassette 244). Here, the sensed variable is the different bar code of the drug-delivery cassette associated with the drug container. In one example, the drug-delivery cassette 244 is installable in the pump assembly 20 of FIG. 1, includes a drug-container holder 242 shown with an installed drug container 212, and includes tubing 246 for making a fluid connection with the pump assembly 20. In one variation, not shown, the sensor 24 is incorporated into the pump assembly 20 to sense (scan) the bar code 234 of the installed drug-delivery cassette 244.

Other types of sensors include, without limitation, RFID (Radio Frequency Identification) sensors, wherein, in one example, an RFID chip is embedded in or on a drug container, a package, a drug-delivery cassette, etc.

In a first design of the first expression of the embodiment of FIG. 1, the controller 26 is programmed to receive a plurality of physiological parameters of the patient 32 during the medical procedure, and the controller 26 is programmed to have the corresponding drug delivery algorithm adjust a flow rate of the drug co-formulation 13 of the operatively-connected one of the drug containers 12 to the patient 32 during the medical procedure as a function of at least the received physiological parameters. It is noted that a flow rate of a drug delivery algorithm may be intermittent or continuous during the medical procedure. In one variation, the controller 26 is programmed to generate at least one alarm signal (such as through wire 48 to alarm 50) based at least on the received physiological parameters. In one modification, the controller 26 is programmed to have the corresponding drug delivery algorithm adjust the flow rate as a function of at least a patient response to a request for a response (such as a time delay for the patient to push a button on a handpiece).

In one example of the first design, the physiological parameters include blood pressure and respiratory rate, wherein the blood pressure is derived using an automated blood pressure cuff 52 operatively connected to the patient 32, and the respiratory rate is derived using pressure measurements from an oral-nasal cannula 54 operatively connected to the patient 32, such blood pressure and respiratory rate derivations being well known to those skilled in the art. In one illustration, a cable (or a tube) 56 separately connects the controller 26 to the sensors 22 and 24 and to the pump assembly 20 and separately connects the controller 26 to the blood pressure cuff 52 and the oral-nasal cannula 54. Other operative connections include, where appropriate and without limitation, wireless communications.

In one illustration of the first design, the controller 26 is adapted to receive a user input (such as through wire 58 from user input device 60) and to modify the adjusted flow rate of the drug co-formulation 13 of the operatively-connected one of the drug containers 12 to the patient 32 during the medical procedure based on the received user input. It is noted that the user is not the patient. In one example, the user input device 60 is a keyboard or a mouse or a monitor touch screen display of a computer, and the alarm 50 is a buzzer of the computer and/or a visual display on the monitor of the computer. Other examples are left to the artisan.

In one modification of the first expression of the embodiment of FIG. 1, tubing 62 carries the drug co-formulation 13 from the drug-container holder 42 to the pump assembly 20, and an intravenous tube 64 carries the drug co-formulation 13 from the pump assembly 20 to the patient 32. In one variation, the drug-container holder 42 includes a spike (not shown) which pierces the drug seal (not shown) of the operatively-connected one of the drug containers 12 when such drug container 12 is received by the drug-container holder 42. The spike includes a drug lumen to carry the drug co-formulation 13 from the drug container 12 to the tubing 62. In one example, the pump assembly 20 includes an intravenous infusion pump such as an intravenous-infusion peristaltic pump.

A second expression of the embodiment of FIG. 1 is for a drug delivery system 10 including a plurality of drug containers 12, 14, 16, and 18, a pump assembly 20, a sensor (two are shown) 22 and 24, and a controller 26. Of course those skilled in the art will recognize that the number of drug containers may vary. The drug containers 12, 14, 16, and 18 each contain a different predetermined drug co-formulation 13, 15, 17, and 19 of predetermined first and second drugs 28 and 30. The first drug 28 has a sedative effect, and the second drug 30 has an analgesic effect. The different predetermined drug co-formulations 13, 15, 17, and 19 include at least four different drug co-formulations 13, 15, 17, and 19. Each of the drug containers 12, 14, 16, and 18 is operatively connectable to the pump assembly 20. One of the drug containers 12 is operatively connected to the pump assembly 20, and the pump assembly 20 is adapted to deliver the drug co-formulation 13 contained in the operatively-connected one of the drug containers 12 to a patient 32 during a medical procedure. The sensor 22 and 24 is adapted to sense a variable associated with each of the drug containers and output a different drug co-formulation identification signal associated with each of the drug containers based on the sensed variable. The controller 26 is operatively connected to the sensor 22 and 24 and to the pump assembly 20. The controller 26 is programmed to identify the drug co-formulation 13 for the operatively-connected one of the drug containers 12 from the associated identification signal and to control the pump assembly 20 to deliver the drug co-formulation 13 of the operatively-connected one of the drug containers 12 to the patient 32 during the medical procedure according to a corresponding drug delivery algorithm which is different for each of the drug containers 12, 14, 16, and 18.

It is noted that the implementations, applications, arrangements, etc. of the first expression of the embodiment of FIG. 1 are equally applicable to the second expression of the embodiment of FIG. 1.

A method of the invention is for delivering drugs to patients during medical procedures using the drug delivery system 10 of the first expression of the embodiment of FIG. 1, wherein the plurality of drug containers 12, 14, 16, and 18 includes at least four drug containers 12, 14, 16, and 18, and wherein the at-least-four drug containers 12, 14, 16, and 18 includes first and second drug containers 12 and 14, and wherein the method includes steps a) through h). Step a) includes choosing the first drug container 12 based on a first medical procedure and an assessment of a patient associated with the first medical procedure. Step b) includes having the sensor 22 and 24 sense the variable associated with the first drug container 12 and output the identification signal associated with the first drug container 12. Step c) includes having the controller 26 automatically determine a first drug delivery algorithm based on the identification signal associated with the first drug container 12. Step d) includes having the controller 26 control the pump assembly 20 to deliver the drug co-formulation 13 of the first drug container 12 to the patient associated with the first medical procedure based at least on the first drug delivery algorithm.

Step e) includes choosing the second drug container 14 based on a second medical procedure and an assessment of a patient associated with the second medical procedure, wherein at least one of the second medical procedure and the patient associated with the second medical procedure is different from the corresponding one of the first medical procedure and the patient associated with the first medical procedure. Step f) includes having the sensor 22 and 24 sense the variable associated with the second drug container 14 and output the identification signal associated with the second drug container 14. Step g) includes having the controller 26 automatically determine a second drug delivery algorithm based on the identification signal associated with the second drug container 14, wherein the second drug delivery algorithm is different from the first drug delivery algorithm. Step h) includes having the controller 26 control the pump assembly 20 to deliver the drug co-formulation 15 of the second drug container 14 to the patient associated with the second medical procedure based at least on the second drug delivery algorithm.

It is noted that the implementations, applications, arrangements, etc. of the first expression of the embodiment of FIG. 1 are equally applicable to the method of the invention.

Several benefits and advantages are obtained from one or more of the method and expressions of an embodiment of the invention. In one example, having different co-formulations (fixed combinations) of a first drug having a sedative effect and a second drug having an analgesic effect allows the user to choose a particular co-formulation best suited to a particular medical procedure and a particular patient, wherein a sensor outputs a different drug co-formulation identification signal associated with each drug container avoiding human error, and wherein a controller automatically determines a particular drug delivery algorithm based on the identified particular co-formulation avoiding the time and human error of having the user determine or choose an algorithm.

While the present invention has been illustrated by a method and several expressions of an embodiment and enablements, applications, etc. thereof, it is not the intention of the applicants to restrict or limit the spirit and scope of the appended claims to such detail. Numerous other variations, changes, and substitutions will occur to those skilled in the art without departing from the scope of the invention. It will be understood that the foregoing description is provided by way of example, and that other modifications may occur to those skilled in the art without departing from the scope and spirit of the appended Claims.

What is claimed is:

1. A drug delivery system comprising:
a) a plurality of drug containers each container of the plurality of containers containing a different predetermined drug co-formulation of a predetermined first drug and a predetermined second drug, wherein the first drug has a sedative effect;
b) a pump assembly, wherein each of the plurality of drug containers is operatively connectable to the pump assembly, and wherein the pump assembly is adapted to deliver the drug co-formulation contained in an operatively-connected one of the plurality of drug containers to a patient during a medical procedure;

c) a sensor adapted to sense a variable associated with each of the plurality of drug containers and output a different drug co-formulation identification signal associated with each of the plurality of drug containers based on the sensed variable; and d) a controller operatively connected to the sensor and to the pump assembly, wherein the controller is programmed to identify the drug co-formulation for the operatively-connected one of the plurality of drug containers from the associated identification signal and to control the pump assembly to deliver the drug co-formulation of the operatively-connected one of the plurality of drug containers to the patient during the medical procedure according to a corresponding drug delivery algorithm which is different for each of the drug containers.

2. The drug delivery system of claim 1, wherein the second drug has an analgesic effect.

3. The drug delivery system of claim 2, wherein the first drug substantially lacks having an analgesic effect, and wherein the second drug substantially lacks having a sedative effect.

4. The drug delivery system of claim 1, wherein the different predetermined drug co-formulations include at least first, second, third, and fourth drug co-formulations.

5. The drug delivery system of claim 1, wherein the first drug co-formulation includes 100 percent of a predetermined first amount of the first drug and includes 0 percent of a predetermined second amount of the second drug, wherein the second drug co-formulation includes from 60 to 90 percent of the first amount of the first drug and includes from 10 percent to 40 percent of the second amount of the second drug, and wherein the third drug co-formulation includes from 10 percent to 40 percent of the first amount of the first drug and includes from 60 percent to 90 percent of the second amount of the second drug.

6. The drug delivery system of claim 1, wherein the first drug is propofol and the second drug is ketamine.

7. The drug delivery system of claim 1, wherein the first drug is propofol and the second drug is remifentanil.

8. The drug delivery system of claim 1, wherein the plurality of drug containers each have substantially a same shape and a different size, wherein the variable is the different size, and wherein the sensor senses the size.

9. The drug delivery system of claim 1, also including a different bar code associated with each of the plurality of drug containers, wherein the variable is the different bar code, and wherein the sensor is adapted to automatically sense the bar code associated with the operatively-connected one of the plurality of drug containers.

10. The drug delivery system of claim 1, also including a different bar code associated with each of the plurality of drug containers, wherein the variable is the different bar code, and wherein the different bar code associated with each of the plurality of drug containers is placed on the associated drug container.

11. The drug delivery system of claim 1, also including a different bar code associated with each of the plurality of drug containers, wherein the variable is the different bar code, and wherein the different bar code associated with each of the plurality of drug containers is placed on at least one of an associated drug-container package and an associated drug-delivery cassette.

12. The drug delivery system of claim 1, wherein the controller is programmed to receive a plurality of physiological parameters of the patient during the medical procedure, and wherein the controller is programmed to have the corresponding drug delivery algorithm adjust a flow rate of the drug co-formulation of the operatively-connected one of the plurality of drug containers to the patient during the medical procedure as a function of at least the received physiological parameters.

13. The drug delivery system of claim 12, wherein the controller is programmed to generate at least one alarm signal based at least on the received physiological parameters.

14. The drug delivery system of claim 12, wherein the controller is adapted to receive a user input and to modify the adjusted flow rate of the drug co-formulation of the operatively-connected one of the plurality of drug containers to the patient during the medical procedure based on the received user input.

15. A drug delivery system comprising:

a) a plurality of drug containers each container of the plurality of containers containing a different predetermined drug co-formulation of a predetermined first drug and a predetermined second drug, wherein the first drug has a sedative effect, wherein the second drug has an analgesic effect, and wherein the different predetermined drug co-formulations include at least four different drug co-formulations;

b) a pump assembly, wherein each container of the plurality of drug containers is operatively connectable to the pump assembly, wherein one container of the plurality of drug containers is operatively connected to the pump assembly, and wherein the pump assembly is adapted to deliver the drug co-formulation contained in the operatively-connected one of the plurality of drug containers to a patient during a medical procedure;

c) a sensor adapted to sense a variable associated with each container of the plurality of drug containers and output a different drug co-formulation identification signal associated with each container of the plurality of drug containers based on the sensed variable; and d) a controller operatively connected to the sensor and to the pump assembly, wherein the controller is programmed to identify the drug co-formulation for the operatively-connected one of the plurality of drug containers from the associated identification signal and to control the pump assembly to deliver the drug co-formulation of the operatively-connected one of the plurality of drug containers to the patient during the medical procedure according to a corresponding drug delivery algorithm which is different for each of the plurality of drug containers.

16. The drug delivery system of claim 15, wherein the controller is programmed to receive a plurality of physiological parameters of the patient during the medical procedure, wherein the controller is programmed to have the corresponding drug delivery algorithm adjust a flow rate of the drug co-formulation of the operatively-connected one of the plurality of drug containers to the patient during the medical procedure as a function of at least the received physiological parameters, and wherein the controller is adapted to receive a user input and to modify the adjusted flow rate of the drug co-formulation of the operatively-connected one of the plurality of drug containers to the patient during the medical procedure based on the received user input.

17. A method for delivering drugs to patients during medical procedures using the drug delivery system of claim 1 wherein the plurality of drug containers includes at least four drug containers, wherein the at-least-four drug containers includes first and second drug containers, and wherein the method comprises:
- a) choosing the first drug container based on a first medical procedure and an assessment of a patient associated with the first medical procedure;
- b) having the sensor sense the variable associated with the first drug container and output the identification signal associated with the first drug container;
- c) having the controller automatically determine a first drug delivery algorithm based on the identification signal associated with the first drug container;
- d) having the controller control the pump assembly to deliver the drug co-formulation of the first drug container to the patient associated with the first medical procedure based at least on the first drug delivery algorithm;
- e) choosing the second drug container based on a second medical procedure and an assessment of a patient associated with the second medical procedure, wherein at least one of the second medical procedure and the patient associated with the second medical procedure is different from the corresponding one of the first medical procedure and the patient associated with the first medical procedure;
- f) having the sensor sense the variable associated with the second drug container and output the identification signal associated with the second drug container;
- g) having the controller automatically determine a second drug delivery algorithm based on the identification signal associated with the second drug container, wherein the second drug delivery algorithm is different from the first drug delivery algorithm; and
- h) having the controller control the pump assembly to deliver the drug co-formulation of the second drug container to the patient associated with the second medical procedure based at least on the second drug delivery algorithm.

18. The method of claim 17, wherein the second drug has an analgesic effect.

19. The method of claim 18, wherein the first drug is propofol and the second drug is ketamine.

20. The method of claim 18, wherein the first drug is propofol and the second drug is remifentanil.

* * * * *